United States Patent [19]

Wong et al.

[11] Patent Number: 5,342,771
[45] Date of Patent: Aug. 30, 1994

[54] FUNCTIONALIZED IMIDAZOLINONE HAPTENS AND PROTEIN CONJUGATES THEREOF USEFUL IN ASSAYS FOR THE DETECTION OF IMIDAZOLINONE HERBICIDES

[75] Inventors: Rosie B. Wong, Piscataway; Zareen Ahmed, Princeton Junction; Milon W. Bullock, Skillman, all of N.J.

[73] Assignee: American Cyanamid Company, Wayne, N.J.

[21] Appl. No.: 23,231

[22] Filed: Feb. 25, 1993

Related U.S. Application Data

[63] Continuation of Ser. No. 621,479, Dec. 3, 1990, abandoned.

[51] Int. Cl.$^5$ .................. C12N 9/96; C12N 11/06; C07K 17/02; A61K 39/385; C07D 401/04; C07D 403/04; C07D 235/04
[52] U.S. Cl. ................. 435/188; 435/964; 530/363; 530/367; 530/380; 530/382; 530/403; 530/404; 530/405; 530/408; 530/409; 546/167; 546/278; 548/325.5
[58] Field of Search ............ 530/363, 367, 380, 382, 530/403–406, 408, 409; 435/188, 964; 546/278, 167; 548/325.5

[56] References Cited

U.S. PATENT DOCUMENTS

| | | | |
|---|---|---|---|
| 4,188,487 | 2/1980 | Los | 548/325.5 |
| 4,297,128 | 10/1981 | Los | 504/277 |
| 4,554,013 | 11/1985 | Los | 504/277 |
| 4,798,617 | 1/1989 | Foster et al. | 65/25.1 |
| 4,798,619 | 1/1989 | Los | 504/156 |

OTHER PUBLICATIONS

Murphy et al (1991) J. Sci. Food Agric. 55:117–140.
*The Merck Index* 11th Edition eds. Budavari et al Merck & Co., Inc, Rahway N.J. 1989 pp. 778–779.
Stidham et al (1990) Pestic. Sci. 29:335–340.
Subramanian et al (1990) "Properties of Mutant Acetolactate Synthases Resistant to Triazolopyrimidine Sulfonamilide" Plant Physiol 94:239–244.
Saari et al (1990) "Mechanism of Sulfonylurea Herbicide Resistance in the Broadleaf Weed, *Kochia Scoparia;*" Plant Physiol 93:55–61.
Johnson et al. J. of Immunoassay, 1(1) (1980) 27–37.
Singh et al. J of Immunoassay, 1(3) (1980) 309–322.
Van Emon et al. Biosis No. 82098096, Anal. Chem. 58(8) 1986 1866–1873.
Kelley et al. Biosis No. 81009970, J. Agric Food Chem. 33(5) 1985, 962–965.
W. Newsom, Pesticide Science and Biotechnology (Oxford: Blackwell Scientific Publications, 1987), 349–352.
J. C. Hall, et al., Weed Technology, 4, pp. 226–234, 1990.
Clark et al. "ELISA Theoretical and Practical Aspects" in E. T. Maggio, Ed. Enzyme Immunoassay (CRC Press, Inc. Boca Raton, Fla. 1980 pp. 167–179.

*Primary Examiner*—Kay K. Kim
*Attorney, Agent, or Firm*—Peggy A. Climenson

[57] ABSTRACT

This invention provides enzyme conjugates, antigens, antibodies and diagnostic test kits used in an enzyme-linked immunosorbent assay method for determining the presence and concentration of imidazolinone compounds.

10 Claims, No Drawings

FUNCTIONALIZED IMIDAZOLINONE HAPTENS AND PROTEIN CONJUGATES THEREOF USEFUL IN ASSAYS FOR THE DETECTION OF IMIDAZOLINONE HERBICIDES

This is a continuation of co-pending application Ser. No. 07/621,479, filed on Dec. 3, 1990 now abandoned.

BACKGROUND OF THE INVENTION

Imidazolinone compounds useful as herbicidal agents are described in U.S. Pat. Nos. 4,188,487; 4,297,128; 4,554,013 and 4,798,619. The imidazolinones are best exemplified by the commercial products imazaquin, imazethapyr, imazamethabenz and imazapyr.

Though imidazolinone compounds gradually degrade in the environment, residues remaining in the soil should be monitored so as to provide the most efficacious weed control while avoiding possible damage to follow crop plants. Current techniques used in determination of imidazolinone compound concentrations in soil, water or plant samples are gas chromatography and high-performance liquid chromatography. However, the high cost of equipment, materials and labor required to perform the tests makes their routine use cost prohibitive. Alternative simple and rapid methods for determining the presence and concentration of imidazolinone compounds in soil, water or plant samples are desired.

Enzyme-linked immunosorbent assay (ELISA) technology has been applied in residue analyses of agrochemicals. W. Newsome, Pesticide Science and Biotechnology (Oxford: Blackwell Scientific Publications, 1987), pp. 349–352, describes the use of an ELISA system for the determination of iprodione in plant samples. ELISA is specific, easy to perform and lends itself to automation and scale-up.

J. C. Hall, et al., Weed Technology, 4, pages 226–234, 1990 describes the advantages of ELISA technology and the development and use of ELISA procedures for trace analysis of 2,4-D and picloram.

The application of ELISA technology requires the use of an antibody specific for the compound of interest. Current ELISA technology utilizes antibodies which are not suitable for the determination of the presence and concentration of imidazolinones. If antibodies against imidazolinone compounds could be prepared, then application of ELISA technology might allow for simple and rapid testing of soil, water or plant samples for imidazolinones.

It is an object of the present invention to provide a simple, efficient and cost effective method for determining the presence and concentration of imidazolinone compounds in soil, water or plant samples.

SUMMARY OF THE INVENTION

The present invention provides an easy, rapid and cost effective enzyme-linked immunosorbent assay (ELISA) method for determining the presence and concentration of imidazolinone compounds.

DETAILED DESCRIPTION OF THE INVENTIONS

The ELISA method of the present invention utilizes: an antigen of an imidazolinone hapten covalently bound to a protein carrier, an animal immunized with the antigen and antibodies produced by the host in response to the antigen, an enzyme conjugate of an imidazolinone covalently bound to an enzyme, detection means for an imidazolinone in a soil, water or plant sample using the antibody and enzyme conjugate in a competitive binding step with such sample and standard colorimetric calibration curve for imidazolinone.

Imidazolinone haptens useful in the preparation of antigens have the structural formula I

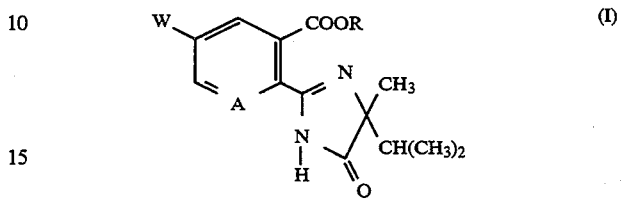

wherein
W is S=C=N— or

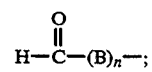

B is $C_2$ alkyl or $C_2$ alkenyl;
n is an integer of 0, 1 or 2;
A is N or CH; and
R is H or $CH_3$.

Preferred formula I haptens which are especially useful in the preparation of antigens are those in which B, n, A and R are as described above for formula I and W is

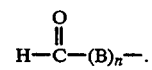

Protein carriers that are suitable for use in the formation of antigens include bovine serum albumin (BSA), human serum albumin (HSA), fibrinogen, ovalbumin (OA), thyroglobulin or keyhole limpet hemocyanin.

The covalently bound hapten-protein antigen is represented by structural formula II

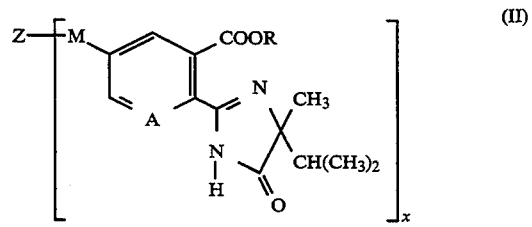

wherein
M is

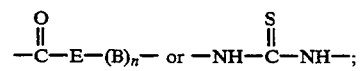

E is —NH—N=CH— or —NH—$CH_2$—;
B is $C_2$ alkyl or $C_2$ alkenyl;
n is an integer of 0, 1 or 2;
A is N or CH;
R is H or $CH_3$;
Z is a protein; and
X is an integer from about 10 to 40.

Preferred formula II antigens useful for antibody production in animals are those in which E, B, n, A, R, Z and X are as described for formula II and M is —E—(B)$_n$—.

Other preferred formula II antigens are those in which M, E, B, n, A, R and X are as described for formula II and Z is BSA.

The covalent bond between the hapten and protein may be formed from the reaction between the aldehyde group of compound I with the hydrazides of proteins such as BSA.

The hapten-protein antigen may also be formed from the reaction between the isothiocyanate group of compound I with the amino groups of proteins such as BSA.

Imidazolinone compounds useful in the preparation of enzyme conjugates have the structural formula III

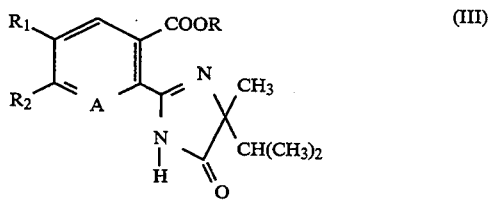

wherein
A is N or CH;
R is H or CH$_3$;
R$_1$ is NH$_2$,

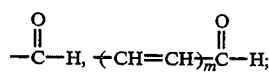

or when taken together with R$_2$ forms a ring in which R$_1$R$_2$ is represented by the structure

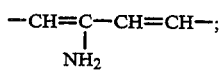

R$_2$ is hydrogen or when taken together with R$_1$ forms a ring in which R$_1$R$_2$ is represented by the structure

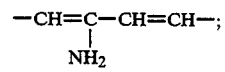

and
m is an integer of 1 or 2.

Enzymes useful in the present invention include those that produce a color change when treated with a substrate. Preferred enzymes are horseradish peroxidase, alkaline phosphatase or urease.

The formula III imidazolinone compounds containing an aldehyde group are covalently bound to the carboxyl groups of the enzymes through the hydrazide to obtain enzyme conjugates having the structural formula IV

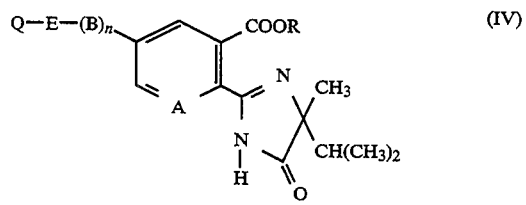

wherein
Q is an enzyme;
E is —NH—N=CH— or —NH—CH$_2$—;
B is C$_2$ alkenyl;
n is an integer of 0, 1 or 2;
A is N or CH; and
R is H or CH$_3$.

Formula III imidazolinone compounds containing a primary amino group are first reacted with thiophosgene to obtain the isothiocyanate. The iothiocyanate is then reacted with enzymes under basic conditions to give enzyme conjugates having the structural formulas V or VI. This reaction scheme is illustrated as follows:

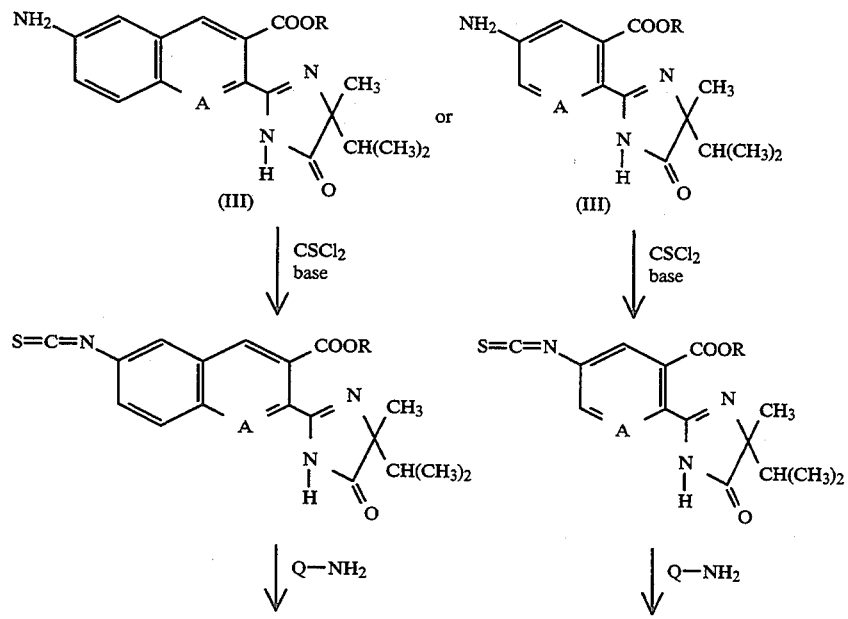

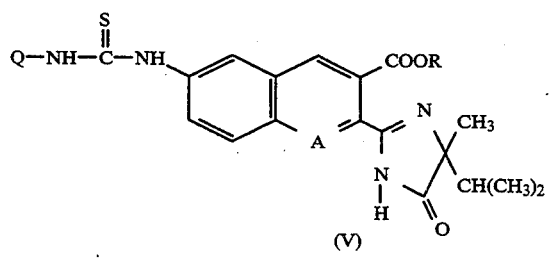

(V)

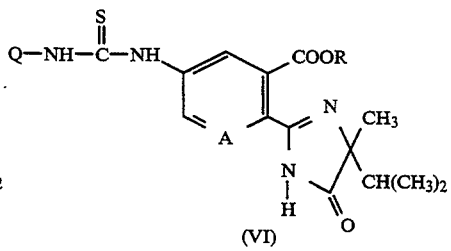

(VI)

wherein
R is H or CH₃;
A is N or CH; and
Q is an enzyme.

The ELISA system of the present invention may be useful for determining the presence and quantity of imidazolinone compounds in either liquid or solid samples such as soil, water or plant samples.

The imidazolinone compounds are represented by structural formula VII

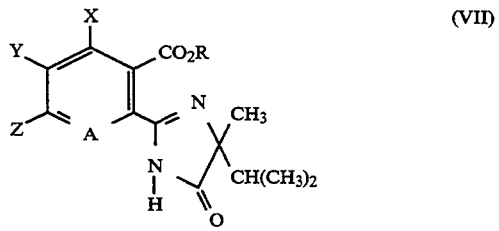

(VII)

wherein
A is N or CH;
R is H or CH₃;
X is H, halogen, methyl or hydroxyl; and
Y and Z are each hydrogen, halogen, C₁–C₄ alkyl, C₁–C₄ alkoxy, C₁–C₄ haloalkyl, nitro, cyano; and when taken together, Y and Z may form a ring in which YZ is represented by —CH=CH—CH=CH—.

The present invention provides an ELISA method which may be useful in determining the presence and concentration of the following commercial products in soil, water or plant samples.

| Product | Chemical Name |
| --- | --- |
| Imazaquin | 2-(4-isopropyl-4-methyl-5-oxo-2-imidazolin-2-yl)-3-quinoline-carboxylic acid |
| Imazethapyr | 5-ethyl-2-(4-isopropyl-4-methyl-5-oxo-2-imidazolin-2-yl)nicotinic acid |
| Imazamethabenz | mixture of methyl 6-(4-isopropyl-4-methyl-5-oxo-2-imidazolin-2-yl)-m-toluate and methyl 2-(4-isopropyl-4-methyl-5-oxo-2-imidazolin-2-yl)-p-toluate |
| Imazapyr | 2-(4-isopropyl-4-methyl-5-oxo-2-imidazolin-2-yl)nicotinic acid |
| Imazamethapyr | 2-(4-isopropyl-4-methyl-5-oxo-2-imidazolin-2-yl)-5-methyl nicotinic acid |
| — | 2-(4-isopropyl-4-methyl-5-oxo-2-imidazolin-2-yl)-5-(methoxymethyl)nicotinic acid |

A diagnostic test kit for the determination of the above described imidazolinone compounds in soil samples utilizes the ELISA method of the present invention. The test kit is compact, portable, easy to use and costs less than currently available tests.

The ELISA method of the present invention is exemplified below. All starting materials are commercially available or prepared according to known procedures.

EXAMPLE 1

Preparation of imidazolinone haptens

To a stirred suspension of methyl 3-hydroxymethyl-6-(4-isopropyl-4-methyl-5-oxo-2-imidazolin-2-yl)-benzoate (5.12 g, 16.86 mmol) in methylene chloride (50 mL, containing 4% pyridine) at room temperature under a nitrogen blanket is added pyridinium chlorochromate (15.54 g, 72.08 mmol). The reaction mixture is stirred for 2 hours at room temperature then quenched by adding ether and filtering through a column of florisil (3 cm×18 cm). The combined filtrates are concentrated in vacuo to give a yellow oil. The oil is purified by flash chromatography on silica gel (200 mL) using ethyl acetate as eluant to obtain methyl 6-(4-isopropyl-4-methyl-5-oxo-2-imidazolin-2-yl)isophthalaldehydate, first hapten, as a colorless oil (1.88 g, 37%); identified by NMR spectral analyses.

A suspension of the above prepared first hapten (1.66 g, 5.5 mmol), (triphenylphosphoranylidene)acetaldehyde (2.05 g, 6.74 mmol) and toluene (50 mL) is heated at reflux temperature for four hours under a nitrogen blanket. The reaction mixture is cooled to room temperature and concentrated in vacuo to obtain a dark gum. The gum is chromatographed on flash silica gel (200 mL) which is eluted with ether. After an initial effluent of 50 mL, 20×25 mL fractions are collected. Fractions 9–14 are pooled and concentrated in vacuo to give a yellow foam (1.17 g). Proton NMR indicates the foam to be a mixture of olefinic products and triphenylphosphine oxide. The mixture is hydrolyzed without further purification by dissolving the foam in a mixture of water (8 mL) and 95% ethanol (2 mL) and adding a solution of 1N potassium hydroxide in methanol (5 mL). The reaction mixture is heated at reflux temperature under nitrogen for 90 minutes. After cooling to room temperature, water (10 mL) is added and the pH is adjusted to 2 with 1N hydrochloric acid. The solvents are removed in vacuo to give a dark brown gum which is dissolved in ethanol (20 mL) and filtered to remove insoluble salts. The gum (1.10 g), obtained from concentration in vacuo of the filtrate, is chromatographed on a C-18 reverse phase semi-prep column, (Dynamax column 30 cm×21.4 mm ID, particle size 8μ). The fractions are eluted with a methanol/-water gradient from 25:75 to 100% methanol over 32 minutes at a flow rate of 13.2 mL/min. Evaporation of the solvents in vacuo gives 5-(2-formylvinyl)-2-(4-isopropyl-4-methyl-5-oxo-2-imidazolin-2-yl)benzoic acid (E), second hapten, as a white powder (102.6 mg, mp 110°–118° C., 6%) and 5-(4-formyl-1,3-butadienyl)-2-(4-isopropyl-4-methyl-5- oxo-2-imidazolin-2-yl)benzoic acid, third hapten, as a yellow powder (112.4 mg). Both haptens are identified by proton NMR spectral analyses.

A fourth hapten is prepared by reacting a solution of 5-dimethoxymethyl-2-(4-isopropyl-4-methyl-5-oxo-2-imidazolin-2-yl)nicotinic acid (3.65 g, 10.9 mmol) with 2N hydrochloric acid (20 mL) with stirring at room temperature for 20 hours. The reaction mixture is basified to pH 3.1 with sodium bicarbonate and concentrated in vacuo to give a gum. The gum is triturated with an acetone/ethanol (1:1) solution, filtered and the filtrate concentrated in vacuo to obtain 5-formyl-2-(4-isopropyl-4-methyl-5-oxo-2-imidazolin-2-yl)nicotinic acid, fourth hapten, as a yellow solid (3.07 g, mp 187°–198° C., 97%). This hapten is identified by IR and NMR spectral analyses. The above reactions are illustrated below.

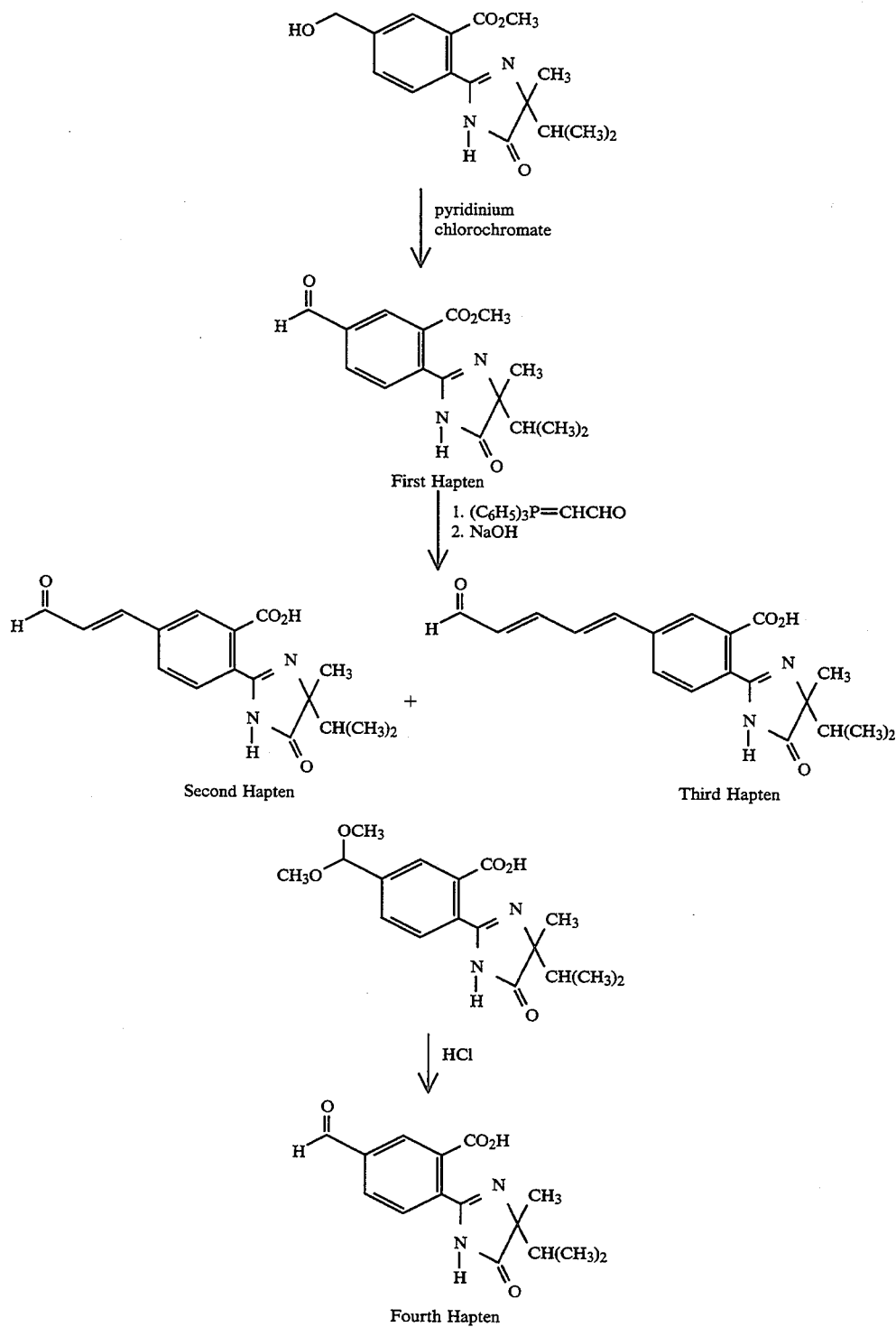

EXAMPLE 2

Antigen Preparation

Bovine serum albumin (BSA) is reacted with about 30 to 50 molar equivalents of hydrazine in the presence of N-hydroxysulfosuccinimide in alkaline solution to generate hydrazide groups from the carboxyl groups of BSA. The hydrazides are then reacted with about 50 to 100 molar equivalents of the above formed second hapten. The reaction mixture is stirred for 3 hours at room temperature then for 18 hours at 4° C. The antigen is then passed through a Sephadex G25 column to remove impurities and the antigen fraction is lyophilized and stored at −20° C. Flow Diagram I illustrates the above reactions.

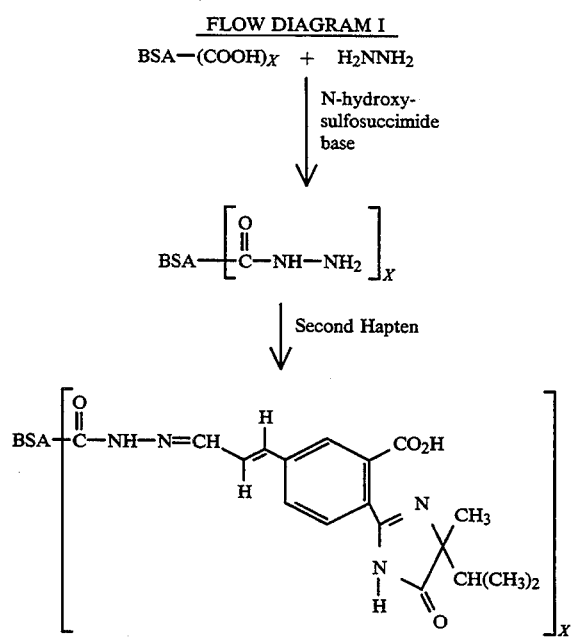

wherein X is an integer from about 10 to 40.

EXAMPLE 3

Antibody Production

The antigen produced in example 2 is dissolved into 0.1M sodium phosphate buffer solution containing 0.14% sodium chloride at pH 7.6 (PBS 7.6). One milliliter of the antigen solution, 0.5 mg antigen per milliliter, is mixed with one milliliter of Freund's complete adjuvant and emulsified. The emulsion is injected perilymph nodal into New Zealand white rabbits at 0.5 mg/rabbit. Three weeks after the initial immunization, 0.25 mg of the antigen in 1 mL of PBS 7.6 is emulsified with 1 mL of Freund's incomplete adjuvant and injected into the rabbits intramuscularly as boosters. The booster injections are introduced every three weeks into the rabbits. After the second boost, blood samples are collected through the ear vein ten days post injection. Serum containing the antibody is harvested from the blood samples and stored.

EXAMPLE 4

Preparation of Enzyme Conjugate

To a solution of 2-(4-isopropyl-4-methyl-5-oxo-2-imidazolin-2-yl)-6-nitro-3-quinolinecarboxylic acid (212 mg, 0,594 mmol) and methanol (100 mL), a 50 mg quantity of 10% palladium on carbon is added under argon. The mixture is allowed to shake under a hydrogen atmosphere (4 psi) for thirty minutes at room temperature, The catalyst is removed by filtration through diatomaceous earth and then the filtrate is concentrated in vacuo. The concentrate is partitioned between 100 mL portions of chloroform and water and the layers are separated. The organic layer is washed three times with water, dried over anhydrous sodium sulfate and concentrated in vacuo to give formula III 6-amino-2-(4-isopropyl-4-methyl-5-oxo-2-imidazolin2-yl)-3-quinolinecarboxylic acid as a yellow solid (170 mg). The purity of this material is determined by TLC on silica gel with chloroform, methanol and acetic acid (220:30:6) elution.

Thiophosgene (0.12 mL, 1.56 mmol) is added to a solution of the above prepared formula III 6-amino-2-(4-isopropyl-4-methyl-5-oxo-2-imidazolin-2-yl)-3-quinolinecarboxylic acid (170 mg, 0.521 mmol) and methanol (25 mL). The reaction mixture is stirred for five minutes at room temperature and then concentrated in vacuo. The residue is redissolved into a small amount of methanol, filtered and the filtrate is added to 25 mL of ether. The resulting precipitate is collected, washed with ether and dried under reduced pressure to give 2-(4-isopropyl-4-methyl-5-oxo-2-imidazolin-2-yl)-6-isothiocyano-3-quinolinecarboxylic acid as a brown powder (190 mg). The product is obtained in the form of a tricyclic anhydride which hydrolyses to the acid in water or during subsequent reaction in aqueous media. The purity of this material is determined by TLC on silica gel with chloroform, methanol and acetic acid (220:30:6) elution.

Horseradish peroxidase hydrazide (HRP-hydrazide, 20 mg) and 2-(4-isopropyl-4-methyl-5-oxo-2-imidazolin-2-yl)-6-isothiocyano-3-quinolinecarboxylic acid (3 mg) are dissolved into a pH 7.5 phosphate buffer. The reaction mixture is stirred for two hours at room temperature, then overnight at 4° C. The enzyme conjugate is purified on a G-25 sephadex column in 30 mM ammonium acetate, lyophilized and stored until used in the immunoassay system of the present invention.

The above reactions are illustrated in Flow Diagram II.

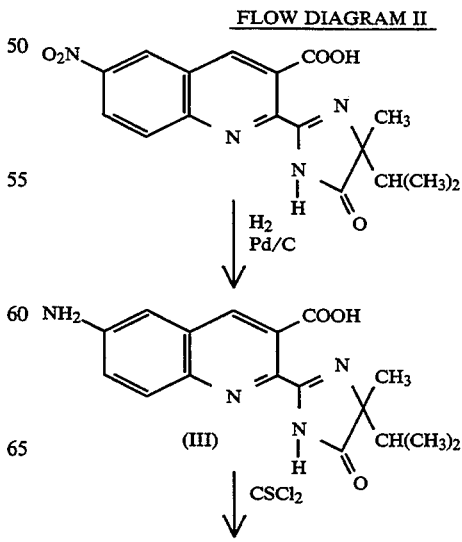

-continued
FLOW DIAGRAM II

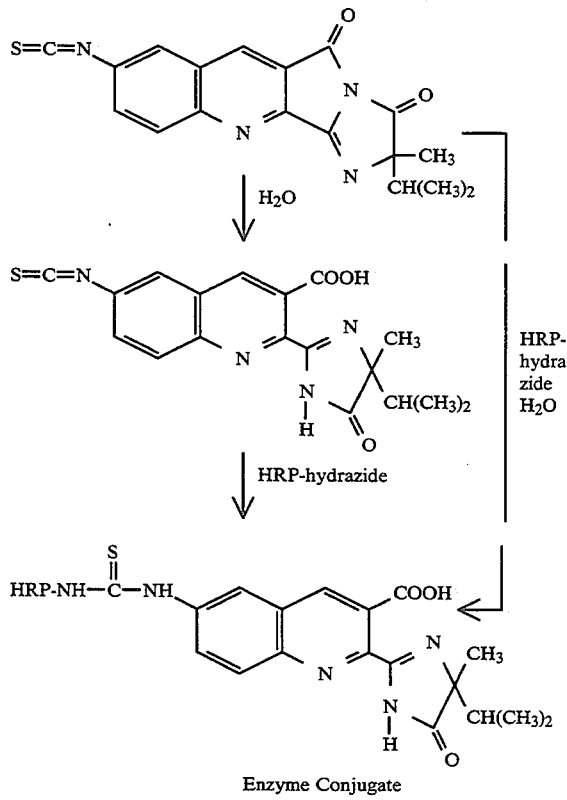

Enzyme Conjugate

EXAMPLE 5
ELISA Method

The antibody and enzyme conjugate prepared above are used to establish an ELISA method for the determination of the presence and concentration of imidazolinones in soil, water or plant samples. A Costar 96 well polystyrene EIA treated flat bottom microwell plate is coated with a constant amount of the antibody in a 0.1N $Na_2CO_3$ buffer. The antibody coated wells are incubated overnight at 4° C., washed with PBS 7.6 buffer containing 0.01% TWEEN® 20, blocked with 5% milk (nonfat dry milk) in PBS 7.6 and incubated 30 minutes at room temperature. Standard solutions having concentrations of imazaquin from 0 to 25 ng per mL are added to the blocked wells followed by the addition of the aforementioned enzyme conjugate.

The wells are incubated for thirty minutes, washed and then a freshly prepared tetramethylbenzidine/hydrogen peroxide substrate solution is added to each well. After ten minutes, readings are taken for each well at 650 nm using a microwell reader.

A standard curve plot having the log of imazaquin concentration on the x-axis and the optical density reading at 650 nm (OD 650) on the Y-axis is used to determine unknown concentrations of imazaquin present in soil, water or plant samples from their OD 650 values.

The OD 650 readings for 7 imazaquin standards are obtained from an ELISA experiment run in triplicate. The means and standard deviations are calculated and are summarized in Table I. The standard curve used to determine unknown imazaquin concentrations is constructed by plotting the mean OD 650 reading versus the logarithm of the standard imazaquin concentration.

TABLE I

| Imazaquin concentration (ng/mL) | OD 650 Reading | Standard Deviation |
| --- | --- | --- |
| 0.39 | 1.452 | 0.015 |
| 0.78 | 1.334 | 0.040 |
| 1.56 | 1.184 | 0.016 |
| 3.12 | 1.064 | 0.027 |
| 6.25 | 0.860 | 0.024 |
| 12.5 | 0.734 | 0.038 |
| 25.0 | 0.564 | 0.010 |

Following the procedure of Example 5 but using the appropriate standard imidazolinone solutions, standard curve plots for other imidazolinones are obtained. These standard curve plots allow for the determination of imidazolinone concentrations in soil, water or plant samples.

EXAMPLE 6
Comparative Soil Analyses

Comparison of the ELISA method of the present invention and a HPLC method is performed with soil samples obtained from the field containing imazaquin. Each sample (100 g) is mixed with 100 mL of 0.5N sodium hydroxide solution for 15 to 60 minutes. The extract solution is then separated from the soil particles by centrifugation and divided into two equal samples for further purification.

The samples for ELISA are further processed by passage through a solid phase cation exchange cartridge which absorbs the imazaquin while allowing the soil to pass through the cartridge. The bound imazaquin is then eluted from the cartridge with a suitable solvent to allow direct analysis by the ELISA method of the present invention using the standard cure plot derived from Table I.

The sample used for the HPLC analysis is purified using standard soil sample techniques. Imazaquin concentrations are then determined by comparing standard HPLC analyses with the sample HPLC analyses.

The results obtained from the above methods are summarized in Table II.

TABLE II

| | ELISA and HPLC analyses of soil samples | |
| --- | --- | --- |
| Sample number | Imazaquin Concentration (ppb) | |
| | HPLC | ELISA |
| 1 | 15.30 | 11.0 |
| 2 | 4.90 | 8.1 |
| 3 | 14.00 | 16.8 |
| 4 | 3.40 | 5.9 |
| 5 | 7.00 | 4.0 |
| 6 | 11.20 | 13.1 |
| 7 | 6.70 | 3.2 |
| 8 | 13.90 | 9.7 |
| 9 | 8.60 | 10.6 |
| 10 | 9.20 | 8.9 |
| 11 | 30.90 | 24.7 |
| 12 | 12.50 | 14.0 |
| 13 | 14.20 | 5.7 |
| 14 | 3.60 | 5.2 |
| 15 | 6.25 | 6.8 |
| 16 | 4.90 | 7.6 |
| 17 | 6.00 | 6.4 |
| 18 | 10.20 | 13.2 |
| 19 | 8.30 | 18.2 |
| 20 | 6.50 | 8.3 |
| 21 | 8.90 | 12.4 |

TABLE II-continued

ELISA and HPLC analyses of soil samples

| Sample number | Imazaquin Concentration (ppb) | |
|---|---|---|
| | HPLC | ELISA |
| 22 | 4.30 | 3.8 |
| 23 | 3.00 | 7.9 |
| 24 | 8.30 | 15.8 |
| 25 | 10.40 | 8.6 |
| 26 | 5.20 | 5.2 |
| 27 | 10.30 | 17.7 |
| 28 | 29.00 | 27.1 |
| 29 | 8.70 | 8.6 |
| 30 | 14.20 | 16.0 |
| 31 | 4.40 | 9.8 |
| 32 | 7.80 | 10.6 |
| 33 | 1.10 | 2.0 |
| 34 | 13.30 | 15.1 |
| 35 | 4.40 | 6.3 |
| 36 | 4.80 | 7.1 |
| 37 | 13.60 | 13.6 |
| 38 | 2.80 | 3.6 |
| 39 | 2.00 | 3.5 |
| 40 | 2.10 | 1.8 |
| 41 | 6.60 | 2.9 |
| 42 | 2.20 | 2.9 |
| 43 | 9.10 | 9.3 |

Pearson correlation coefficient = 0.831.

As shown in the above table, the enzyme-linked immunosorbent assay method of the present invention is useful for the determination of imazaquin concentrations in a number of soil samples.

EXAMPLE 7

Cross-Reactivity Studies

The cross reactivity of the antibody with imidazolinone compounds, imidazolinone metabolites and other commonly found agrochemicals is determined using the procedure of example 5. The concentration of a compound which produces a 50% reduction of absorbance caused by the enzyme conjugate binding to a known amount of antibody is defined as the $I_{50}$ value (50% inhibition concentration). The $I_{50}$ values from the cross-reactivity studies are in Table III.

TABLE III

| CROSS-REACTIVITIES | |
|---|---|
| Compound | $I_{50}$ (ng/mL) |
| Imazaquin | 10.7 |
| Imazethapyr | 18.5 |
| Imazamethabenz | 33.2 |
| Imazapyr | 149.0 |
| 3-[(1-Carbamoyl-1,2-dimethylpropyl)carbamoyl]quinaldic acid | >5,000 |
| Methyl 3-[(1-carbamoyl-1,2-dimethylpropyl)carbamoyl]-2-quinolinecarboxylate | >5,000 |
| 2-[(1-Carbamoyl-1,2-dimethylpropyl)carbamoyl]-3-quinoline-carboxylic acid | >5,000 |
| 1,3-Dihydro-α-isopropyl-α-methyl-1,3-dioxo-2H-pyrrolo[3,4-b]-quinoline-2-acetamide | >5,000 |
| Butachlor | >100,000 |
| Chlorsulfuron | >100,000 |
| Atrazine | >100,000 |
| Alachlor | >100,000 |
| Paraquat | >100,000 |
| Pendimethalin | >100,000 |

As shown in the above table, the antibody of the present invention is useful in the determination of imidazolinone concentrations even in the presence of imidazolinone metabolites and/or other non-imidazolinone compounds.

Test kit

A diagnostic field test kit for the analysis of imidazolinones in samples by using the ELISA method of the present invention comprises:
1. An antibody specific to imidazolinones bound on a solid phase,
2. An enzyme conjugate which comprises an imidazolinone covalently bound to an enzyme,
3. Standards containing known amounts of the said imidazolinone,
4. Buffer solutions for diluting reagents and washing the solid phase in reagent 1,
5. Substrate solution for eliciting a measurable color change from the enzyme conjugate in measurable reagent 2, and
6. A means for colorimetric measurement.

What is claimed:

1. An antigen for producing an antibody against an imidazolinone having the structure

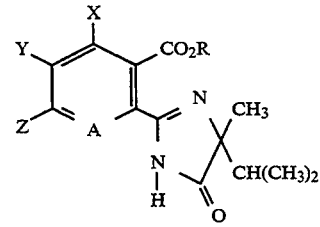

wherein
A is N or CH;
R is H or $CH_3$;
X is H, halogen, methyl or hydroxyl; and
Y and Z are each independently hydrogen, halogen, $C_1$-$C_4$ alkyl, $C_1$-$C_4$ alkoxy, $C_1$-$C_4$ haloalkyl, nitro, cyano; or Y and Z are taken together to represent —CH=CH—CH=CH—;
which comprises an imidazolinone hapten having the structural formula

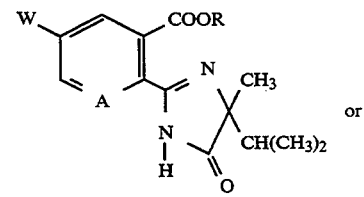

or

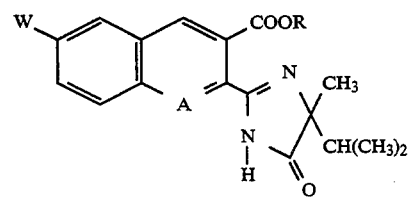

wherein
W is

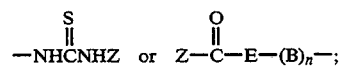

E is —NH—N=CH— or —NH—CH₂—;
B is $C_2$ alkyl or $C_2$ alkenyl;
n is an integer of 0, 1 or 2;
Z is a protein;
A is N or CH; and
R is H or $CH_3$.

2. The antigen according to claim 1 wherein the imidazolinone is selected from the group consisting of imazaquin, imazethapyr, imazamethabenz, imazapyr imazamethapyr and 2-(4-isopropyl)-4-methyl-5-oxo-2-imidazolin-2-yl)-5-(methoxymethyl)nicotinic acid.

3. The antigen according to claim 1 wherein the protein is selected from the group consisting of bovine serum albumin, human serum albumin, fibrinogen, ovalbumin, thyroglobulin and keyhole limpet hemocyanin.

4. An antigen according to claim 1 having the formula

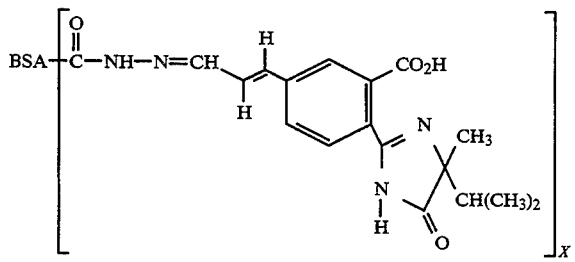

wherein X is an integer from about 10 to 40 and BSA is bovine serum albumin.

5. An enzyme conjugate comprising an imidazolinone having the structural formula

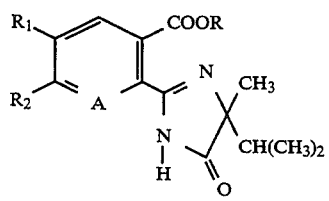

wherein
A is N or CH;
R is H or $CH_3$:
$R_1$ is NHQ,

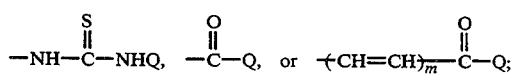

$R_2$ is hydrogen; or $R_1$ and $R_2$ are taken together to represent

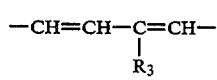

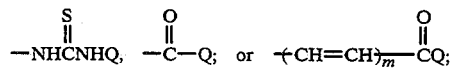

m is an integer of 1 or 2; and wherein Q is an enzyme.

6. The enzyme conjugate according to claim 5 wherein the enzyme is selected from the group consisting of horseradish peroxidase, alkaline phosphatase and urease.

7. The enzyme conjugate according to claim 5 having the structural formula

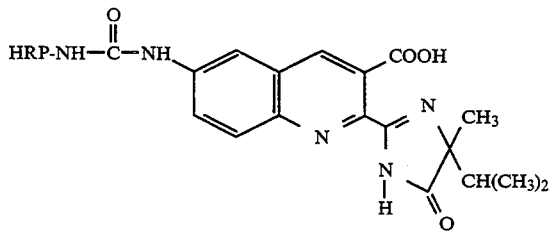

wherein HRP is horseradish peroxidase.

8. An imidazolinone hapten having the structural formula

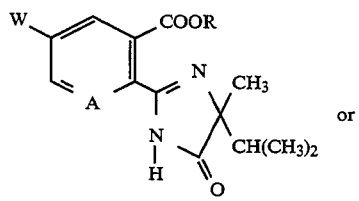

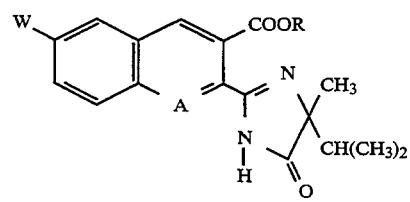

wherein
W is S=C=N— or

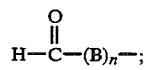

B is $C_2$ alkyl or $C_2$ alkenyl;
n is an integer of 0, 1 or 2
A is N or CH: and
R is H or $CH_3$; with the proviso that when A is N then n is not 0.

9. A hapten according to claim 8, 5-(2-formylvinyl)-2-(4-isopropyl-4-methyl-5-oxo-2-imidazolin-2-yl)benzoic acid.

10. A hapten according to claim 8, selected from the group consisting of methyl 6-(4-isopropyl-4-methyl-5-oxo-2-imidazolin-2-yl)isophthalaldehydate and 5-(4-formyl-1,3-butadienyl )-2-(4-isopropyl-4-methyl-5-oxo-2-imidazolin-2-yl) benzoic acid.

* * * * *